US007931857B2

(12) United States Patent
Ramaccioni

(10) Patent No.: US 7,931,857 B2
(45) Date of Patent: Apr. 26, 2011

(54) MIXING CHAMBER FOR THE APPLICATION OF A SURFACE ACTION AGENT BY VAPOUR AND RELATED DISPENSING DEVICE

(76) Inventor: Fabrizio Ramaccioni, Città di Castello PG (IT)

( * ) Notice: Subject to any disclaimer, the term of this patent is extended or adjusted under 35 U.S.C. 154(b) by 674 days.

(21) Appl. No.: 11/579,870

(22) PCT Filed: Mar. 25, 2005

(86) PCT No.: PCT/IB2005/051038

§ 371 (c)(1),
(2), (4) Date: Nov. 8, 2006

(87) PCT Pub. No.: WO2005/107966

PCT Pub. Date: Nov. 17, 2005

(65) Prior Publication Data

US 2007/0157805 A1 Jul. 12, 2007

(30) Foreign Application Priority Data

May 10, 2004 (IT) .............................. PG2004A0015

(51) Int. Cl.
*A61L 9/015* (2006.01)

(52) U.S. Cl. ................................ 422/4; 134/36; 95/149

(58) Field of Classification Search ........ 422/4; 134/35, 134/36, 37; 95/149
See application file for complete search history.

(56) References Cited

U.S. PATENT DOCUMENTS

| | | | | | |
|---|---|---|---|---|---|
| 2,571,575 | A | * | 10/1951 | Holmes | 239/9 |
| 2,624,618 | A | * | 1/1953 | Gelles et al. | 239/9 |
| 3,467,314 | A | * | 9/1969 | Grubb | 239/138 |
| 4,414,037 | A | * | 11/1983 | Friedheim | 134/35 |
| 5,261,949 | A | | 11/1993 | Schilling et al. | |

FOREIGN PATENT DOCUMENTS

| | | | |
|---|---|---|---|
| EP | 0 923 985 | A | 6/1999 |

* cited by examiner

*Primary Examiner* — Sean E Conley
(74) *Attorney, Agent, or Firm* — Nixon & Vanderhye P.C.

(57) ABSTRACT

A mixing chamber, for the application of a disinfecting agent by vapour, exploits the combined and combined and synergistic action of the mixed product and comprises a calming zone, at least one section (15) for inletting vapour in said calming zone, at least one section (7) for outletting vapour, and for directing it to an applicator nozzle, characterized in that it comprises a spray nozzle (5) inletting a disinfecting agent under pressure in said calming zone, drawing it from a suitable tank (3).

3 Claims, 2 Drawing Sheets

MIXING CHAMBER FOR THE APPLICATION OF A SURFACE ACTION AGENT BY VAPOUR AND RELATED DISPENSING DEVICE

This application is the US national phase of international application PCT/IB2005/051038 filed 25 Mar. 2005, which designated the U.S. and claimed priority of IT PG2004A000015 filed 10 May 2004, the entire contents of each of which are hereby incorporated by reference.

The present invention relates to a mixing chamber for the application of a surface action agent by vapour, and related dispensing device, for the cleaning of surfaces and the concomitant application of a disinfecting, phytopharmaceutical, disinfecting agent or the like.

As it is known, a widespread method for cleaning surfaces which, owing to various reasons, cannot be directly treated with water jets, is that of using water vapour obtained, in the various commercially available machines, by heating water to boiling temperature in a suitable boiler.

Such a method, by virtue of the heat and of the dissolving action of the vapour, as well as of its mechanical action, ensures a cleaning of the treated surface but not its complete disinfection. Attempts have been made to combine a disinfecting agent or the like to the vapour, e.g., by adding the agent directly into the boiler tank along with the water, yet with the result of precipitating a sizeable fraction of product as bottom residue together with the calcareous deposits. Moreover, there ensues the chemical alteration of the agent, subjected to an excessive exposition to heat.

According to other solutions, it was preferred to mix the agent with water vapour at the applicator nozzle, without however attaining a good mixing level.

U.S. Pat. No. 5,261,949-A discloses a mixing chamber for mixing a surface action agent into a gas carrier.

The technical problem underlying the present invention is to provide a mixing chamber and a related dispensing device making use of it overcoming the drawbacks mentioned with reference to the known art.

This problem is solved by a dispensing device and by a method for dispensing a surface action agent according to the appended independent claims The main advantage of the dispensing device and of the related method according to the present invention lies in allowing a uniform mixing of the surface action agent in the vapour under pressure to be ejected via the applicator nozzle, without degrading or wasting the agent itself.

It is understood that the device and the device according to the invention could advantageously be used for the application of a disinfecting and generally hygienizing agent on washable surfaces. Hence, the device will be particularly suitable for household cleaning, industrial cleaning, cleaning of public environments and of equipments of various nature.

Likewise, the device could advantageously be used in agriculture, for the superficial application of disinfectants, disinfecting, defoliants, herbicides and plant protection products.

The herbicidal action benefits from the use of said device owing to the synergy between the application of the vapour and the application of the herbicide agent. The vapour contributes to the herbicidal action and fosters the superficial absorption of localized action agents.

Moreover, it is understood that the device and the method according to the invention will be suitable for the superficial application of any surface action agent. In fact, the vapour is applied by condensation, covering in a particularly uniform manner the surface to be treated. Thus, the diffusion of the superficial agent is just as uniform.

Hereinafter, the present invention will be described according to a preferred embodiment thereof, given by way of example and without limitative purposes, with reference to the annexed drawings, wherein.

Figure 1:
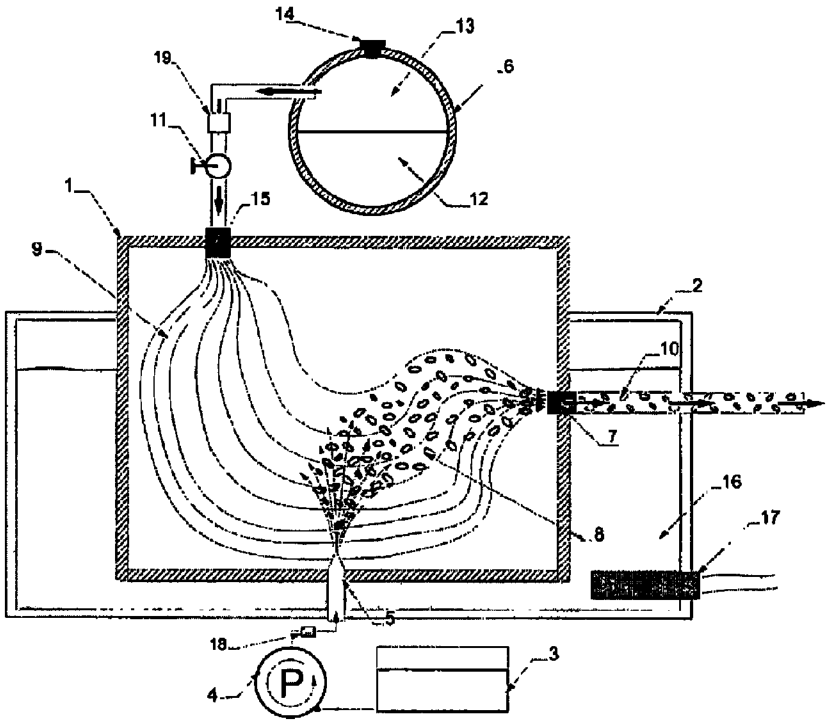
FIG. 1 shows a schematic sectional view of the main components of a dispensing device with the mixing chamber according to the invention.
Figure 2:
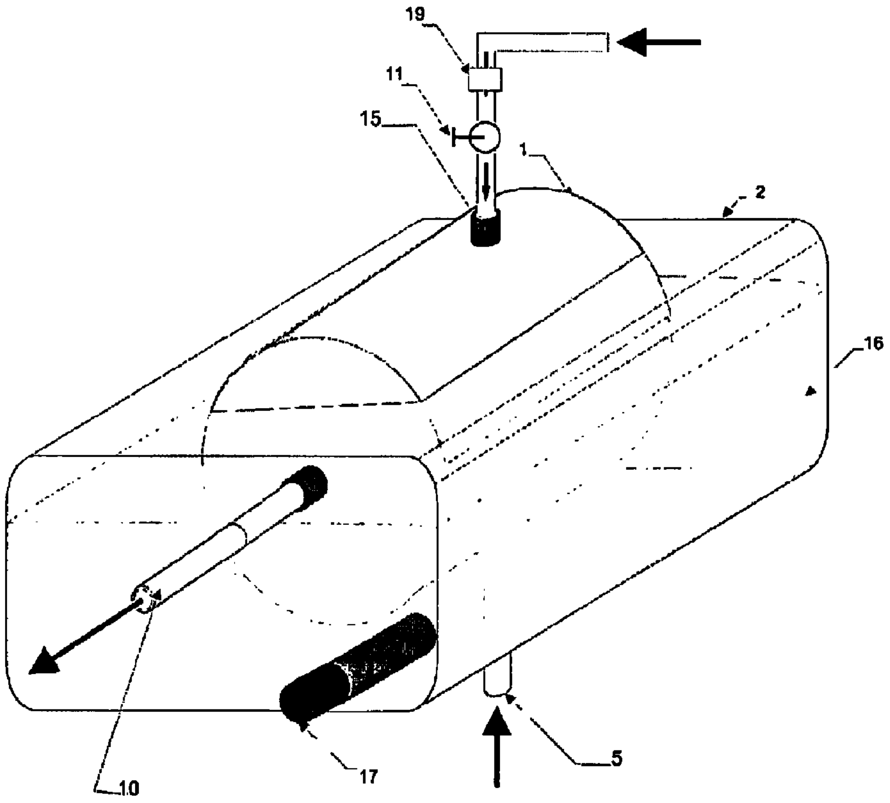
FIG. 2 shows a schematic perspective view of a mixing chamber according to the invention.

With reference to FIGS. 1 to 2, the dispensing device according to the present embodiment, in particular a hygienizing device for surfaces, comprises a heat-resistant container 1 where the mixing occurs, a jacket 2 housing said container 1, where diathermic oil 16 or another thermal carrier (heat-carrying) fluid is heated to keep the heat-resistant container 1 heated at a preset temperature. The heating occurs by virtue of a cartridge-shaped resistance 17 inserted inside the jacket 2.

The container 1-jacket 2 assembly forms a mixing chamber, fed by a vapour inlet The container 1-jacket 2 assembly forms a mixing chamber, fed by a vapour inlet section represented by a coupling 15, from which it is inletted the vapour from a boiler 6, which in turn comprises a water inlet cap 14, a chamber-connecting duct having a flow rate adjuster 11 and a first solenoid valve 19 for opening and closing the vapour inlet duct.

The mixing chamber further comprises a spray nozzle for the inletting of a disinfecting agent pumped under pressure by a pump 4 connected to a suitable tank 3 of disinfecting agent, via a second solenoid valve 18 closing and opening the inlet duct of the liquid disinfecting agent.

By effect of the inletting with nebulization, inside of the mixing chamber there are formed nebulized particles 8 of disinfecting agent, dispersed in a calming zone of the chamber. Inside said zone, a vapour flow 9 occurs; the vapour crosses the mixing chamber to an outlet and dispatch section, consisting of an outlet collector 7 for the vapour+disinfecting agent mixed product.

Via a pipe 10, said product reaches the vapour-applying nozzle.

The operation of the above-illustrated two-phase mixing chamber for the application of a disinfecting agent by vapour can be described as follows:

Inside the mixing chamber, via the coupling 15 and upon activation of the first solenoid valve 19, it is introduced water vapour coming from the boiler 6 where the water 12 is brought to boil, thereby turning into vapour 13.

Concomitantly, by activating the second solenoid valve 18, a liquid disinfecting agent 8 under pressure drawn from the tank 3 by the pump 4 is injected by the spray nozzle 5 into the mixing chamber. Thus, a monovariant two-phase system is generated that exits the collector 7 and, via the pipe 10, is transported to the user, that will consist of an array of nozzles suitable for the application of the disinfecting mixture on any surface.

The jacket 2, according to the present preferred embodiment, forms a sort of watertight box inside which there is diathermic oil; the resistance 17, controlled by a respective thermostat, not shown, keeps the oil temperature at values ideal to keep the mixing chamber at the right temperature, preventing the inletted vapour from condensing at the contact of the disinfecting liquid and of the colder walls, such a condition being crucial for a good two-phase vapour-disinfecting mixing.

By acting on the flow rate adjuster 11, the quantity of water vapour 13 entering the mixing chamber is adjusted; accordingly, the vapour-disinfecting ratio is modified to adapt it to use needs.

The constant temperature of the mixing chamber may also be obtained by inserting a cartridge-shaped resistance therein, or locating the chamber itself into contact with the vapour-producing boiler, or using any other heating system suitable therefor.

The geometric shape of said chamber and the position of the orifices is designed so as to have minimal turbolences therein, thereby optimizing the outflow of hygienizing and disinfecting mixture. The positioning of the mixing chamber is not binding, and may be near the boiler 6 or in any other point of the pipe in which vapour flows. The shape and the various construction details, orifice number and shape included, may vary in any one invention suitable therefor.

Figure 3:
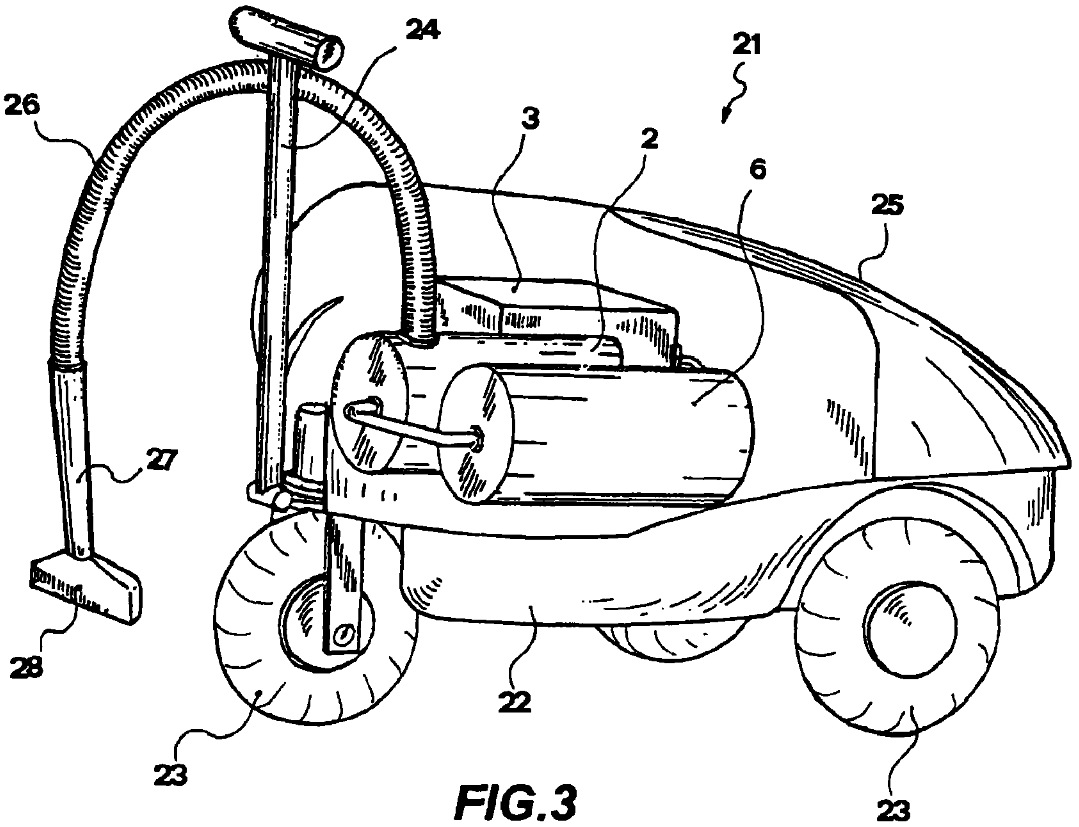
FIG. 3 shows a partially sectional view of a dispensing device according to the invention.
Figure 4:
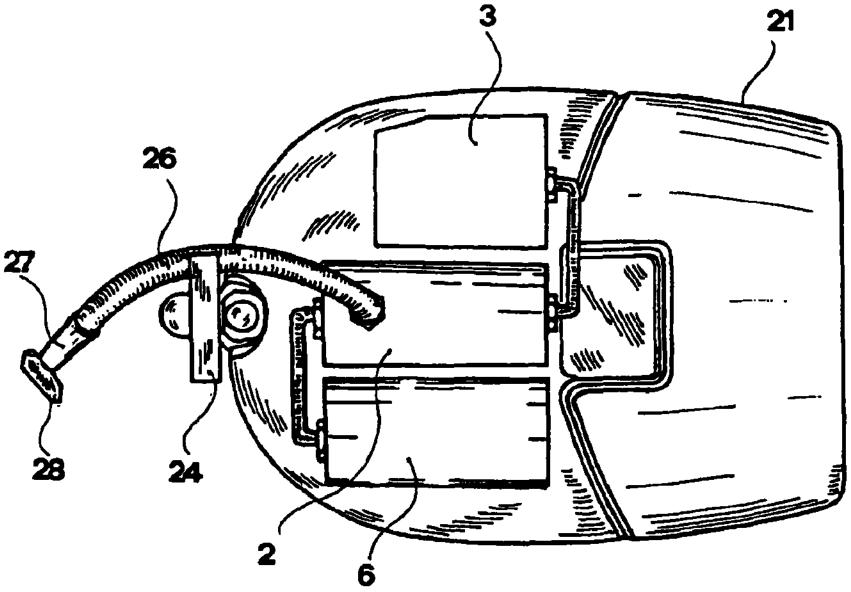
FIG. 4 shows a plan view of the device of FIG. 3.

With reference to FIGS. 3 and 4, it can be appreciated how the above-described mixing chamber may be incorporated in a hygienizing device 21; the latter comprises a base 22 on wheels 23 and a drag handle 24. The device 21 further comprises a case 25 housing the mixing chamber, i.e., the jacket 2 with the heat-resistant container 1 thereinside. In addition, the former houses the boiler 6 and the tank 3 for the disinfecting agent, suitably connected as described above.

Moreover, the device 21 comprises a flexible hose 26 carrying the mixed product to a lance 27 ending in one or more applicator nozzles incorporated in a cleaning member 28.

Object of the technical solution underlying the present invention is to combine the washing power of the vapour to the disinfecting power of a specific product. This result is attained from the combined and synergistic action of the water vapour and the disinfecting in the two-phase mixing chamber. In addition to the shape of the chamber and the distribution of the orifices, the perfect mixing is attained also via the preheating of the mixing chamber. By virtue of this contrivance, it is possible to distribute on any surface the hygienizing vapour, which by condensing forms a disinfecting film allowing to attain an optimal result.

The above-described device is intended to find employ in all those situations where, besides cleaning, a disinfecting treatment by contribution of a specific product is required. This device is of very simple construction; for its optimal operation, it may preheat its mixing chamber where the vapour and the disinfecting agent mingle, so as to prevent the excessive formation of condensate and to have a carrying of the hygienizing product without altering the chemical features thereof.

However, it is understood that the thermostating of the mixing chamber may be attained also with equivalent systems, provided they be such as to keep the chamber environment sufficiently hot to prevent vapour degradation.

Such a thermostating might be also attained by suitably adjusting the inletting of vapour in the chamber, as well as its inlet temperature.

To the above-described mixing chamber and to the related hygienizing device a person skilled in the art, in order to satisfy further and contingent needs, could effect several further modifications and variants, all however encompassed in the protective scope of the present invention, as defined by the appended claims.

The invention claimed is:

1. Method for forming a surface action agent film on a surface, comprising the steps of:
- inletting vapour in a calming zone of a mixing chamber;
- inletting a surface action agent in said calming zone, thereby forming a mixed product in the mixing chamber, the mixed product comprising said surface action agent and said vapour;
- pre-heating the mixing chamber to a predetermined and constant temperature to prevent the inletted vapour from condensing inside the mixing chamber, thereby producing a two-phase mixed product;
- outletting the mixed product; and
- dispensing the mixed product on said surface, condensation of the vapour on the surface forming the surface action agent film.

2. Method according to claim 1, wherein said pre-heating step comprises enveloping the mixing chamber with oil or other diathermic fluid contained in a watertight jacket.

3. Method according to claim 1, wherein said surface action agent is a hygienizing agent, a disinfecting agent, a defoliant agent, a herbicide agent or a phytopharmaceutical product.

* * * * *